(12) United States Patent
Yeung (10) Patent No.: US 8,664,002 B2
(45) Date of Patent: Mar. 4, 2014

(54) METHOD AND SYSTEM FOR COLLECTING CELLS FOLLOWING LASER MICRODISSECTION

(75) Inventor: Richard Yeung, West Vancouver (CA)

(73) Assignee: Motic China Group Co., Ltd. (CN)

( * ) Notice: Subject to any disclaimer, the term of this patent is extended or adjusted under 35 U.S.C. 154(b) by 1723 days.

(21) Appl. No.: 11/914,151

(22) PCT Filed: May 19, 2006

(86) PCT No.: PCT/CA2006/000838
§ 371 (c)(1),
(2), (4) Date: Jan. 15, 2008

(87) PCT Pub. No.: WO2006/122434
PCT Pub. Date: Nov. 23, 2006

(65) Prior Publication Data
US 2008/0199929 A1      Aug. 21, 2008

(30) Foreign Application Priority Data

May 20, 2005   (CN) .......................... 2005 1 0034838

(51) Int. Cl.
*G01N 1/18* (2006.01)
*C12Q 1/68* (2006.01)
*G01N 1/30* (2006.01)
*G01N 1/04* (2006.01)
*G01N 1/40* (2006.01)

(52) U.S. Cl.
CPC .. *G01N 1/04* (2013.01); *G01N 1/30* (2013.01); *G01N 1/4077* (2013.01); *C12Q 1/68* (2013.01); *C12Q 1/6806* (2013.01)
USPC ......... 436/177; 435/6.1; 435/40.5; 435/40.52

(58) Field of Classification Search
CPC ......... G01N 1/04; G01N 1/30; G01N 1/4077; C12Q 1/68; C12Q 1/6806
USPC ........................ 435/40.5, 40.52, 6.1; 436/177
See application file for complete search history.

(56) References Cited

U.S. PATENT DOCUMENTS 5,985,085 A * 11/1999 Baer et al. ...................... 156/285
5,998,129 A   12/1999 Schutze et al.
(Continued)

FOREIGN PATENT DOCUMENTS

WO         98/35216        8/1998
WO   WO 2004/068104 A2 *  8/2004

OTHER PUBLICATIONS

Emmert-Buck, et al. 'Laser Capture Microdissection Science Nov. 8, 1996: vol. 274 No. 5289 pp. 998-1001.*

(Continued)

*Primary Examiner* — Shafiqul Haq
*Assistant Examiner* — Gary E Hollinden
(74) *Attorney, Agent, or Firm* — Timothy M. McCarthy (57) ABSTRACT

A method of collecting target regions from a target object is described. The method in one embodiment comprises mounting a negatively-charged membrane on a first side of a substrate, mounting a target object on the membrane, positioning a collection material adjacent to the target object, and passing a laser beam from a second side of the substrate, through the substrate, the membrane, and the target object, to dissect target regions from the prepared tissue section, whereby the dissected target regions adhere to the collection material. In another embodiment, the present invention is a system for collecting target regions from a target object. In one embodiment, the system comprises a substrate having a first side and a second side, a negatively-charged membrane adhered to the first side of the substrate, and a collection material mountable adjacent to the membrane. In another embodiment, the system further comprises an inverted microscope, a stage for holding the substrate over the microscope, a generator operable to generate a laser beam to pass through the substrate from the second side and to dissect target regions from a target object mounted on the membrane, whereby the dissected target regions adhere to the collection material. In the preferred embodiments, the target objects are tissues and the target regions are cells.

14 Claims, 5 Drawing Sheets

(56) References Cited

U.S. PATENT DOCUMENTS

| | | | |
|---|---|---|---|
| 6,121,428 A * | 9/2000 | Blank et al. ................... 530/413 |
| 6,468,657 B1 * | 10/2002 | Hou et al. ..................... 428/403 |
| 6,469,779 B2 | 10/2002 | Baer et al. |
| 6,690,470 B1 * | 2/2004 | Baer et al. ..................... 356/417 |
| 6,743,601 B1 | 6/2004 | Bonner et al. |
| 6,758,961 B1 * | 7/2004 | Vogel et al. ................ 205/777.5 |
| 6,780,584 B1 * | 8/2004 | Edman et al. ................ 435/6.19 |
| 6,783,937 B1 * | 8/2004 | Hou et al. ..................... 435/6.12 |
| 7,001,550 B2 * | 2/2006 | van Reis ......................... 264/48 |
| 8,535,876 B2 * | 9/2013 | Wesner ............................. 435/4 |
| 2001/0001574 A1 | 5/2001 | Baer et al. |
| 2003/0148295 A1 * | 8/2003 | Wan et al. ......................... 435/6 |
| 2006/0023201 A1 * | 2/2006 | Malekafzali .................... 356/36 |
| 2012/0058483 A1 * | 3/2012 | Parr et al. ..................... 435/6.12 |

OTHER PUBLICATIONS

High-performance RNA for gene expression analysis; by Qiagen.com. 2004; total 40 pages.*

Schutze and Lahr (Nature Biotechnology; 16:737-742; 1998).*

M. Bohm, et al., Membrane-Based Laser Microdissection in Molecular Oncology, Onkologie, 1999; 22:296-301.

Kolble, The LEICA microdissection system: Design and application, J. Mol. Med., 2000, pp. B24-B25.

* cited by examiner

METHOD AND SYSTEM FOR COLLECTING CELLS FOLLOWING LASER MICRODISSECTION

PRIORITY

This application is a national-phase entry of PCT/CA2006/000838, filed May 19, 2006, and claims priority from Application No. 200510034838.3, filed in the Republic of China on May 20, 2005, the disclosure of which is incorporated herein in its entirety.

BACKGROUND OF THE INVENTION

The present invention relates to a new method and system for non-contact collection of cells or other target regions following laser microdissection from tissue sections, tissue-derived cell preparations, other biologically-derived materials, or non-biological materials that have been mounted onto a specially-prepared slide.

In the field of life science, selecting and successfully collecting homogeneous cells of interest without contamination from heterogeneous tissue samples is a precondition for the accurate and specific isolation and characterization of biologically relevant molecules that pertain to the normal, diseased, or malignant state of the cell population.

The earliest technique for microdissection separation was using a glass needle or other tool to separate target regions mechanically from tissue sections, an operation achieved by hand or assisted by a manipulator. This method possessed many disadvantages, including a high degree of difficulty, high time consumption, low efficiency and precision, high demand for skills of the operator, and low bioactivity of separated biological samples caused by mechanical injury.

In 1996, the laser was introduced to precisely dissect microscopic target regions of interest. Since that time, laser microdissection systems have been used for dissection and separation in the biological and medical field. Laser microdissection systems are characterized by excellent effectiveness of dissection, high efficiency of collection, and timely completion; there are minor adverse effects on the subsequent analysis of the genes or proteins. So far, the techniques of separation and collection based on laser microdissection involve laser capture microdissection technique (LCM), laser pressure catapulting technique (LPC), sticky membrane transfer technique, and a collecting technique using the force of gravity. These distinct methods for collection are the core techniques of laser microdissection system.

The laser capture microdissection technique utilizes a low-power infrared laser to melt a special thermoplastic film over target regions of tissue sections (for example, Bear et al., Laser Capture Microdissection Method and Apparatus, PCT No. PCT/US98/02388). The melted film expands after absorbing the laser energy, and adheres to target regions underneath. When the film is moved away, target regions attached to the film are separated successfully from tissue sections. The main disadvantages of this technique include mechanical damage on biological samples during separation and low precision because the film may also stick cells around target regions.

The laser catapulting technique uses a laser beam to dissect target regions, followed by the laser being defocused to strike the glass which creates a photo-acoustic pressure wave that causes the dissected target regions to catapult, overcoming gravity, into a sample collector (for example, U.S. Pat. No. 5,998,129 to Schutze et al., Method and Device for the Contactless Laser Assisted Microinjection, Sorting and Production of Biological Objects Generated in a Planar Manner). Disadvantages for this technique include the additional time required to defocus the laser, then re-focus on the sample, and the possibility that the UV laser beam may strike the middle of the cells, where the DNA and RNA may be altered by the laser.

The sticky membrane transfer technique utilizes a special sticky membrane to stick dissected target regions and collect the sample after the dissection (for example, M. Böhm et al., *Membrane-Based Laser Microdissection in Molecular Oncology*, ONKOLOGIE, 2000; 22:296-301). The membrane used in this method may lead to higher cost.

Collecting by the force of gravity must be based on the upright microscope (Koelble et al., *The Leica Microdissection System: Design and Applications*, J. MOL MED, 78 (7): B24-25, 2000). The dissected target regions fall down by the force of gravity directly into a collecting container located beneath the objective lens and microscope slide (which has to be turned upside down to place it on the microscope stage before beginning the procedure).

There is a need for a method and apparatus to collect cells following laser microdissection that avoids the problems of the prior art. The present invention meets this need.

SUMMARY OF THE INVENTION

Briefly, and in accordance with the foregoing, the present invention in one embodiment is a method of collecting target regions from a target object. The method in one embodiment comprises mounting a negatively-charged membrane on a first side of a substrate, mounting a target object on the membrane, positioning a collection material adjacent to the target object, and passing a laser beam from a second side of the substrate, through the substrate, the membrane, and the target object, to dissect target regions from the prepared tissue section, whereby the dissected target regions adhere to the collection material. In the preferred embodiment, the target objects are tissues and the target regions are cells.

In another embodiment, the present invention is a system for collecting target regions from a target object. In one embodiment, the system comprises a substrate having a first side and a second side, a negatively-charged membrane adhered to the first side of the substrate, and a collection material mountable adjacent to the membrane. In another embodiment, the system further comprises an inverted microscope, a stage for holding the substrate over the microscope, a generator operable to generate a laser beam to pass through the substrate from the second side and to dissect target regions from a target object mounted on the membrane, whereby the dissected target regions adhere to the collection material. In the preferred embodiment, the target objects are tissues and the target regions are cells.

BRIEF DESCRIPTION OF DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE PREFERRED EMBODIMENTS OF THE INVENTION

While the invention may be susceptible to embodiments in different forms, there is shown in the drawings, and herein will be described in detail, specific embodiments with the understanding that the present disclosure is to be considered an exemplification of the principles of the invention, and is not intended to limit the invention to that as illustrated and described herein.

The novel method and apparatus of the present invention consists of the non-contact transfer of target regions from a target object, such as cells in a mounted tissue section on a prepared slide, by electrostatic repulsion of the small mass of the target regions by the static electric charge of the much larger dielectric membrane onto which the tissue sections are mounted, and the subsequent electrostatic cling of the laser-microdissected target regions to a polar collection material, such as an agar gel, positioned above the prepared slide. The electrostatic repulsion of the laser-dissected small mass effectively acts as a propulsion actuator of the target regions, overcoming the force of gravity sufficiently long enough for the target regions to reach and adhere to the agar gel in the collection container suspended above the prepared slide and the tissue sections, cells, or other material attached to it.

Figure 1:
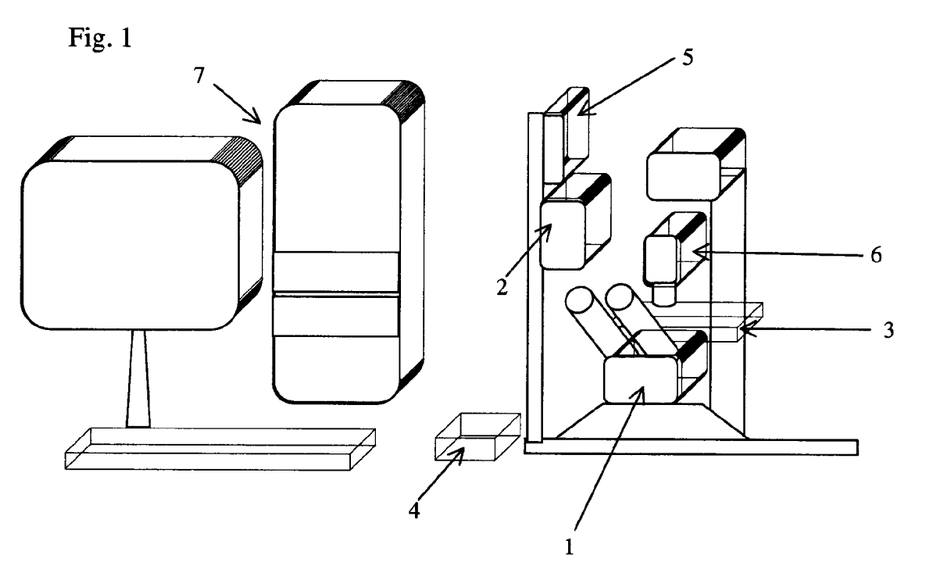
FIG. 1 is an overall view of a laser microdissection system of the preferred embodiment of the present invention.

As demonstrated in FIG. 1, the laser microdissection system in the present invention includes an inverted biological microscope 1, a laser generator 2, a motorized stage 3, a three-axis joystick 4, a central controller 5, a camera 6, and a computer 7.

Figure 3A:
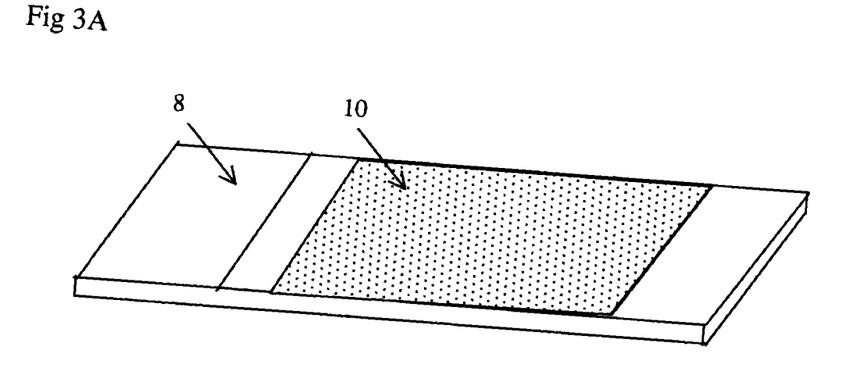
FIG. 3A is a top perspective view of a membrane-coated slide of the preferred embodiment of the present invention.

As shown in FIG. 3A, a negatively-charged membrane 10 is attached to a first side of a substrate 8. Substrate 8 in the illustrated embodiment is a standard glass microscope slide, approximately 1.0 mm thick. Substrate 8 can alternatively be a silica-based substrate, such as wafer, or can be a biochip, a polymer, or some other material for holding the target object.

Membrane 10 is preferably a material having a high dielectric capable of sustaining a large electrostatic charge suitable for repulsive actuation and propulsion of small, negatively-charged masses from the first side of substrate 8. The material of membrane 10 preferably highly absorbs UV, near-UV, and violet radiation (approximately 199 to 440 nm). Membrane 10 preferably transmits visible light (approximately 450 to 760 nm) at least 90 percent, most preferably at least 95 percent.

Membrane 10 is preferably a thin polyimide film, such as those materials sold under the trade name Kapton® by E.I. du Pont de Nemours and Company, most preferably the types HN, VN, and FN. Membrane 10 can also be made of another polymeric material, such as a thermoplastic, a thermosetting polymer, an elastomer, a non-conducting polymer, or combinations of these materials. Suitable materials include, but are not limited to, polyethylene, polypropylene, polyvinyl chloride, styrene, polyurethane, polycarbonate, polyethylene terephthalate, cellulose, gelatin, chitin, polypeptides, polysaccharides, polynucleotides, and combinations of these materials. Membrane 10 can also be made of a ceramic hybrid polymer, a phospine oxide, or a chalcogenide. Membrane 10 is cut into a rectangular size a little smaller than the size of substrate 8.

Membrane 10 preferably has a thickness of about eight um, to allow a laser beam to pass through without obvious energy loss, thereby ensuring the efficiency of dissection and facilitating the electrostatic collection.

Figure 2A:
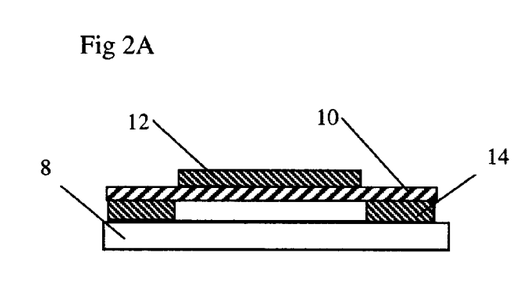
FIG. 2A is a side elevation view of a membrane, glass slide, and adhesive of the preferred embodiment of the present invention.
Figure 2B:
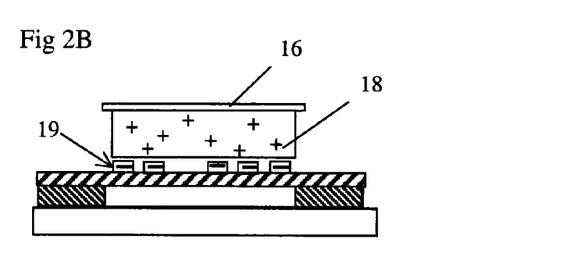
FIG. 2B is the combination illustrated in FIG. 2A, placed adjacent a collection material of the preferred embodiment, and showing microdissected tissue cells.

The periphery of membrane 10 is adhered to substrate 8 by an adhesive 14, as shown in FIG. 2A. (Note that the center of membrane 10 is left without adhesive 14.) In the case where the target object 12 is a prepared tissue sample, adhesive 14 is preferably a light-curable, preferably UV-curable, medical grade adhesive that is compatible with post-collection analysis of biological materials. In the illustrated embodiment, the isolation and identification of nucleotides (DNA, RNA, iRNA, etc.) is contemplated, so adhesive 14 must be chosen so as not to interfere chemically with such a post-microdissection analysis. Adhesives 14 can be, by way of example and not by way of limitation, acrylic-based, silicon-based, or cyano-acrylate-ester-based.

In the case where adhesive 14 is an ultraviolet-curing adhesive, the combination of membrane 10, substrate 8, and adhesive 14 is radiated under the ultraviolet for about fifteen seconds and then stored in a clean environment for further application.

Figure 3B:
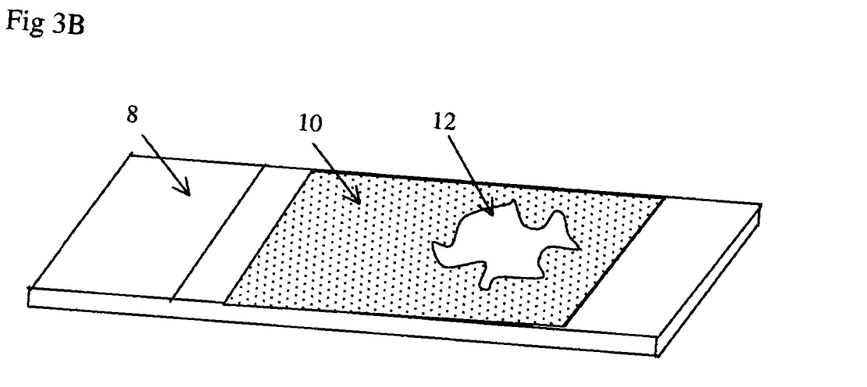
FIG. 3B is a view of the slide of FIG. 3A having a tissue mounted thereon.

As shown in FIGS. 2A and 3B, a target object 12 is mounted directly on the center of membrane 10. In the illustrated embodiment, target object 12 is a prepared tissue section, such as a frozen section or paraffin-embedded section. Conventional treatment and staining of the tissue section could be accomplished before laser dissection.

Target object 12 is then positioned over the inverted microscope 1 shown in FIG. 1. A laser beam generated by the laser generator 2 of FIG. 1 is passed through the objective of microscope 1 and through substrate 8, and ultimately dissects the target object 12 together with the attached membrane 10. The user of the preferred embodiment, seeing the magnified target object 12 through the eyepiece or eyepieces of microscope 1, manipulates the laser beam using the joystick 4 of FIG. 1 to accomplish microdissection.

Figure 4A:
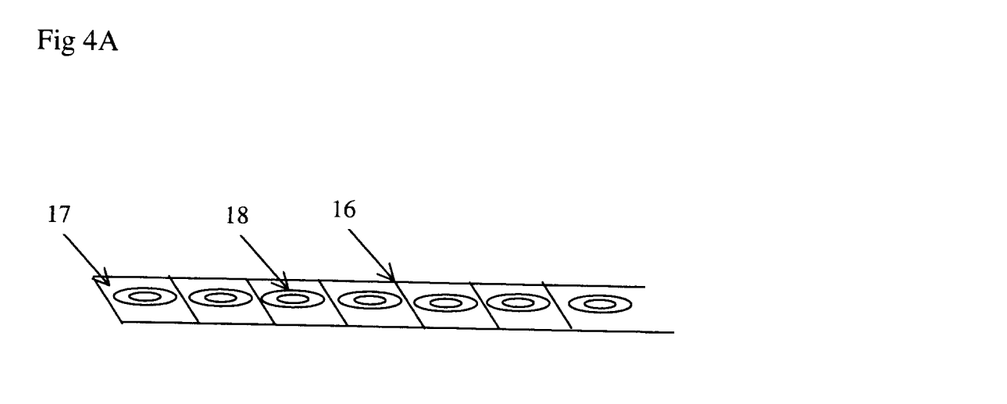
FIG. 4A is a top perspective view of the strip of collection devices of the preferred embodiment of the present invention.
Figure 4B:
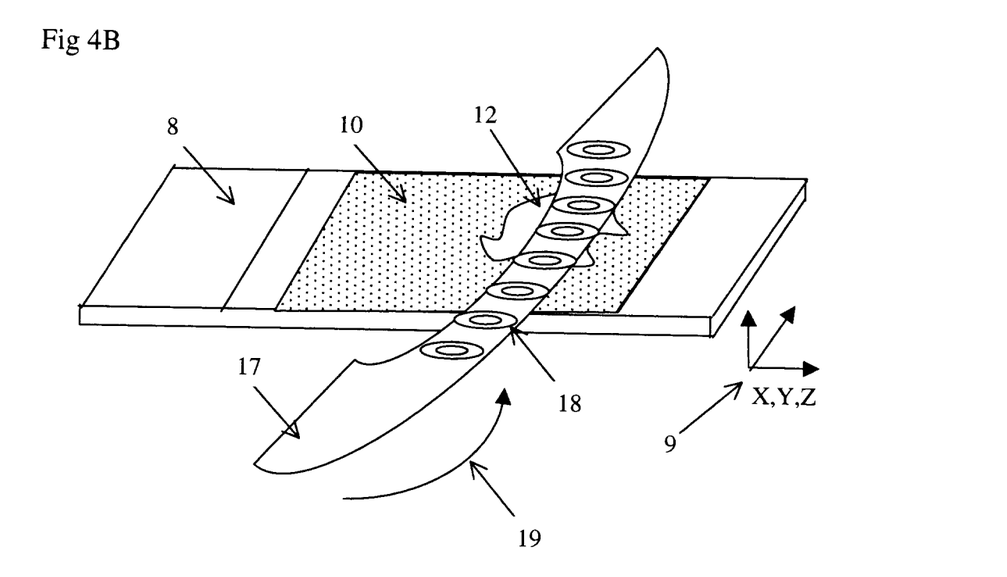
FIG. 4B is a top perspective view of the strip of FIG. 4A placed over the slide of FIG. 3B.

In the illustrated embodiment, a strip 17 on stage 3 holds a series of centrifugal tube caps 16 containing a collection material 18, as shown in FIGS. 4A and 4B. Collection material 18 is either a positively-charged material or a polar material having both positive and negative charges. Collection material 18 is preferably a phosphate-buffered saline (PBS) with agar, preferably a 1.0 to 2.5 weight-to-volume percent concentration, most preferably 1.5 percent agar. This material will be a gel at room temperature but will melt to liquid at 45 to 50 C.

In the illustrated embodiment, an agar gel is prepared by dropping agar solution in PBS into the caps 16 until the solution is solidified. The surface of agar gel is slightly lower than the brim of the cap 16. The caps 16 containing agar gel are packed and stored at 4 C overnight.

Strip 17 is then manipulated to position a single cap 16 directly above target object 12, as shown in FIG. 4B. In the case where target object 12 is a prepared tissue section, the gap distance is less than 0.5 mm. Strip 17 in the preferred embodiment is be operated manually but can also be operated by mechanical components.

Figure 2C:
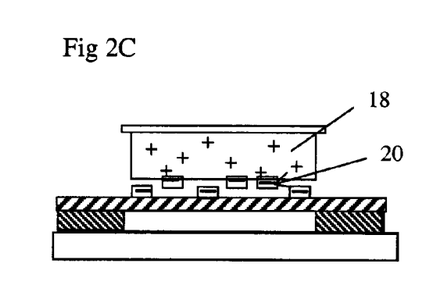
FIG. 2C is the combination illustrated in FIG. 2B, showing the microdissected cells adhering to the positively-charged collection material.
Figure 5:
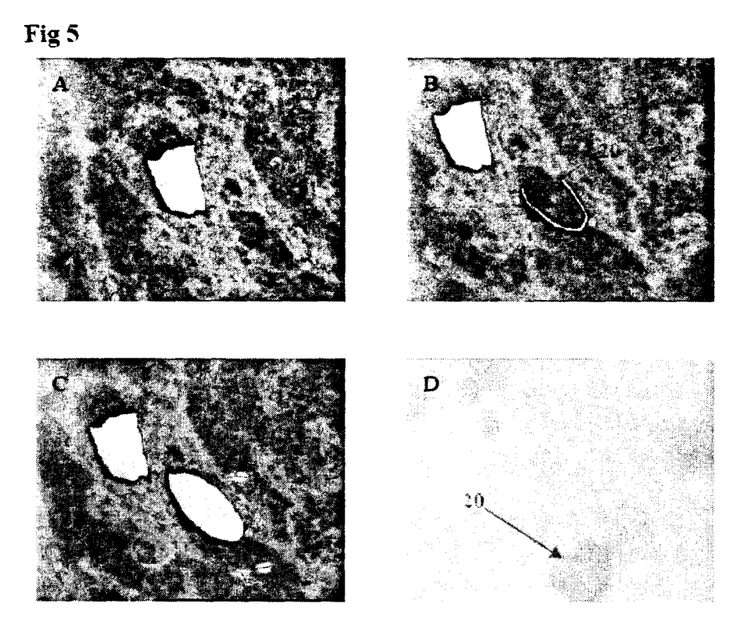
FIG. 5A is an image of a tissue sample, taken through an inverted microscope before a round of laser microdissection.
FIG. 5B is an image of the tissue sample of FIG. 5A, taken during laser microdissection.
FIG. 5C is an image of the tissue sample of FIG. 5B, demonstrating that the dissected target region is repelled off the tissue section by the electrostatic force.
FIG. 5D is an image of the tissue sample of FIG. 5C, demonstrating that after laser microdissection the dissected target region is captured on the surface of the agar gel collection material.

The operator manipulates the laser beam produced by the laser generator 2 of FIG. 1, using the joystick 4 of FIG. 1, to separate regions of interest within the target object. The user determines which of the regions of interest to dissection, and uses the laser beam to dissect target regions 20 and their attached membrane 10. When the operator dissects target regions 20 to separate those target regions 20 from the rest of target object 12, dissected target regions 20 and the attached negatively-charged membrane 10 are attracted by the collection material 18 just above the target object 12, and are captured on the surface of the collection material 18 in the cap 16 (as shown in FIGS. 2C and 5D).

A researcher can observe the number of target regions 20 which are attached on the surface of the agar gel 18 and evaluate the efficiency of dissection. A number of target regions 20 of a particular type can be collected in a particular cap 16. The operator can then manipulate strip 17 to place a different cap 16 over target object 12, and can then collect target regions 20 of a different type, but from the same tissue, in that cap 16. Alternatively, of course, a different substrate 8 with a different target object 12 can be inserted for collection of target regions 20 of the same type but from a different source. In the illustrated embodiment, there are eight caps 16 in strip 17, but caps 16 can be used singly, placed in an array, or oriented in any other manner.

Figure 2D:
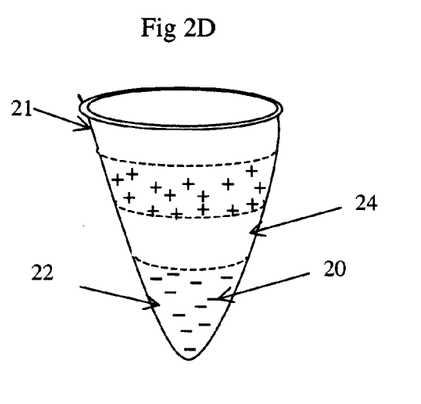
FIG. 2D is a side view of a centrifugal tube containing lysis buffer and microdissected cells with the negatively-charged membrane.

After target regions 20 have been dissected and collected, caps 16, carrying target regions 20 on the surface of collection material 18 (as illustrated, the agar gel), are removed carefully from strip 17, and connected tightly with their corresponding centrifugal tube bodies 21 as shown in FIG. 2D. The user shakes tube bodies 20 manually or using a laboratory shaker, to contact the appropriate lysis buffer 22 added previously in each tube body 21 to target regions 20, so that target regions 20 stuck on the surface of the agar gel 18 will fall down into lysis buffer 22 and wait for a subsequent biological analysis.

An automatic microdissection function can be used after outlining all target regions 20 to be dissected. The height of strip 17 can be adjusted and the distance between the frozen tissue section 12 and the surface of agar gel 18 is shortened as small as possible, but without directly contacting agar gel 18 to tissue section 12. The agar gel 18 is prepared as mentioned previously. The user outlines the target regions 20 using joystick 4, but without generating a laser beam. Computer 7 captures the movements and stores those movements. The user then actuates the automatic microdissection function and the computer controls the movements of the laser beam generated by generator 2 to microdissect target regions 20. The dissected target regions 20 will be automatically repelled and ultimately above 80 percent of the dissected target regions 20 can be successfully captured on the surface of the agar gel 18 in caps 16.

Features and characteristics of the present laser microdissection system will be illustrated by the following examples, to which the present invention is not to be limited.

Example 1

In this example, a special inverted 20× fluorite objective in microscope 1 can be used for laser microdissection. This objective has a high transmission of a 337 nm ultraviolet laser beam. The researcher can use about 61 percent of the total laser power to cut freshly-prepared frozen tissue sections and an approximately six um wide cut line may be achieved.

For the purpose of downstream DNA analysis of tumor cells, eight urn thick frozen tissue sections derived for hepatic carcinoma are prepared in the pathological lab following the standard treatment and mounted on the polyimide film 10 on the regular one mm thick glass slides 8.

Frozen sections 12 are fixed in 70 percent ethanol for 15 seconds, dipped in water, stained by a conventional method (e.g. hematoxylin), and dipped into 50 percent, 70 percent and 100 percent ethanol, sequentially. The sections 12 are exposed to air to dry for five minutes. The slides can now be used at once (even if they are somewhat wet) or deep frozen at −80 C.

In this example, the researcher can outline large target regions 20 through the 20× objective, which could be identified with the help of a histochemical color reaction, a morphological visible change, or fluorescent dye labeling. Since a single target region 20 has approximately one to two hundred cells, about ten to twenty pieces of dissected target regions 20 would meet the cell number requirement for DNA analysis.

Subsequently, caps 16 containing the dissected target regions 20 are fitted into a 0.5 ml micro-centrifugal tube 21, and by shaking, dissected objects 20 fall into the cell lysis liquid 22 in the tube 21, and the subsequent DNA extraction and PCR (polymerase chain reaction) for special genes can follow a conventional method used in molecular biological labs. Alternatively, agar gel electrophoresis may be used to obtain the result of DNA analysis.

Example 2

In this example, a special 100× oil immersion objective can be used on microscope 1 to isolate and collect several cell groups of interest, even single cell. The collected cells can be extracted and subsequentially subjected to the downstream RNA analysis of tumor cells.

As described as the Example 1, approximately eight um thick frozen sections derived from breast carcinoma tissue are prepared onto the polyimide film 10 on a 0.17 mm thin coverslip instead of a 1.0 mm glass slide, which is special to match 100× oil immersion objective. Frozen sections 12 are treated as described as Example 1.

Before microdissection, frozen sections 12 are disposed upright on the motorized stage 3 in the present laser microdissection system. A small amount of immersion oil, such as anisol, is added on the lens surface of the 100× oil immersion objective, and the 100× objective is elevated toward the back of the glass coverslip as closely as possible. After observing and outlining all separate cell groups of interest, the researcher can operate the laser microdissection system to automatically isolate the target objects 20. With the electrostatic repulsive force, the isolated cells 20 can easily be captured onto the agar gel 18 in the collection caps 16. During laser microdissection in this example, only 60 percent of the total laser power is used to efficiently isolate cells from frozen tissues, and therefore a two um wide fine cut line is obtainable.

Sample images of tissue samples 12 and dissected target regions 20 are shown in FIGS. 5A through 5D. FIG. 5A is an image of a tissue sample 12, taken through an inverted microscope 1 before a round of laser microdissection. FIG. 5B shows the tissue sample 12 during laser microdissection. FIG. 5C shows the tissue sample 12, with the dissected target regions 20 being repelled off the tissue section 12 by electrostatic force. FIG. 51) show the tissue sample 12, with the dissected target regions 20 having been captured on the surface of the agar gel collection material 18.

Because of the low number of the collected cells of interest, certain special RNA extraction reagents can be used to promote the result of RNA analysis. The procedure to extract RNA can be done in a conventional manner with an RNA extraction reagent. After PCR, the special gene expression from the RNA extractant (such as c-myc, P53, P27, etc., which is associated with the carcinogenesis) can be analyzed by means of some molecular biological method.

While preferred embodiments of present invention are shown and described, it is envisioned that those skilled in the art may devise various modifications of the present invention without departing from the spirit and scope.

The invention that is claimed is:

1. A method of analysis, comprising:
    attaching a first side of a negatively-charged membrane to a first side of a substrate;
    mounting a target object to a second side of the membrane;
    positioning a collection material adjacent to the target object so that the target object is between the second side of the membrane and the collection material, wherein the collection material is a polar material or a positively-charged material;
    dissecting a target region from the target object by passing a laser beam from a second side of said substrate, through the substrate, the membrane, and the target object.

2. The method of claim 1, wherein said collection material is phosphate buffered saline and agar gel.

3. The method of claim 1, wherein the target object is at least one of a tissue section, a tissue-derived cell preparation, a biologically-derived material, and a non-biological material.

4. The method of claim 3, wherein said target region comprises cells and said method further comprises extracting DNA from said cells.

5. The method of claim 4, further comprising at least one of a polymerase chain reaction and electrophoresis.

6. The method of claim 4, further comprising exposing said cells to a lysis buffer.

7. The method of claim 1, wherein said membrane is a high-dielectric film.

8. The method of claim 7, wherein said film comprises at least one of a thermoplastic, a thermosetting polymer, an elastomer, and a non-conducting polymer.

9. The method of claim 8, wherein said film comprises at least one of a polyethylene, a polypropylene, a polyvinyl chloride, a styrene, a polyurethane, a polyimide, a polycarbonate, a polyethylene terephthalate, a cellulose, a gelatin, a chitin, a polypeptide, a polysaccharide, and a polynucleotide.

10. The method of claim 1, wherein said attaching a first side of a negatively-charged membrane step comprises adhering said membrane to said substrate with an adhesive.

11. The method of claim 10, wherein said adhesive is light-curable.

12. The method of claim 1, wherein said substrate is chosen from the group consisting of a glass slide, a polymeric slide, a silica wafer, and a biochip.

13. The method of claim 1, wherein the dissecting a target region from the target object step further comprises selecting the target region within the target object using a microscope.

14. The method of claim 13, wherein the microscope comprises an inverted microscope.

* * * * *